United States Patent
Christensen (10) Patent No.: US 6,197,068 B1
(45) Date of Patent: *Mar. 6, 2001

(54) PROSTHETIC FOOT SIMULATING TOE ROTATION

(75) Inventor: Roland J. Christensen, 192 E. 100 North, Fayette, UT (US) 84630

(73) Assignee: Roland J. Christensen, Fayette, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/213,035

(22) Filed: Dec. 16, 1998

Related U.S. Application Data (63) Continuation-in-part of application No. 08/906,287, filed on Aug. 4, 1997, now Pat. No. 5,944,760.

(51) Int. Cl.$^7$ ........................................................ A61F 2/66
(52) U.S. Cl. ................................................. 623/55; 623/52
(58) Field of Search ........................................... 623/53–55

(56) References Cited

U.S. PATENT DOCUMENTS

| | | |
|---|---|---|
| 2,036,830 | 4/1936 | Rowley . |
| 2,640,200 | 6/1953 | Wisbrun . |
| 4,547,913 | 10/1985 | Phillips . |
| 4,822,363 * | 4/1989 | Phillips .................................. 623/53 |
| 5,037,444 * | 8/1991 | Phillips .................................. 623/55 |
| 5,181,933 * | 1/1993 | Phillips .................................. 623/55 |
| 5,376,141 * | 12/1994 | Phillips .................................. 623/55 |
| 5,387,246 | 2/1995 | Phillips . |
| 5,443,528 * | 8/1995 | Allen ...................................... 623/55 |
| 5,653,767 * | 8/1997 | Allen et al. ............................ 623/55 |
| 5,944,760 * | 8/1999 | Christensen ........................... 623/55 |

* cited by examiner

*Primary Examiner*—Bruce Snow
(74) *Attorney, Agent, or Firm*—Thorpe, North & Western, LLP (57) ABSTRACT

A prosthetic foot, having a forefoot member and a heel member, is comprised of two separate members forming opposite halves of the foot generally about the longitudinal axis of the foot for simulating natural rotation of the toes of a real foot. The forefoot member of the foot forms a resilient arc extending from a fixture member to a toe position and has an attachment portion, a curvilinear spring portion, an arch portion, and a toe portion. The heel member extends between the forefoot member and a heel position and has an attachment portion and a heel portion. The heel member is preferably attached to the forefoot member by wrapping the members with a resin impregnated fiber. The foot preferably has a rib-and-groove type connection between the forefoot and heel members for preventing the forefoot and heel portions from sliding and rotating with respect to each other and thus prevents shear stress form being placed on the fibers holding the members together. The foot has a fixture member for attachment to a socket for receiving a stump of an amputee and may include an angle adjustment for adjusting the angle of the foot members with respect to the ground. The foot may include a secondary heel member in addition to the heel member, or primary heel member for supporting the primary heel member.

17 Claims, 5 Drawing Sheets

PROSTHETIC FOOT SIMULATING TOE ROTATION

This is a continuation-in-part application of U.S. patent application Ser. No. 08/906,287, filed Aug. 4, 1997, now U.S. Pat. No. 5,944,760, issued Aug. 31, 1999.

BACKGROUND OF THE INVENTION

1. Field of the Invention

The present invention relates to a prosthetic foot that simulates toe rotation. More particularly, the present invention relates to a prosthetic foot having two separate members forming opposite halves of the foot generally about the longitudinal axis of the foot or having a substantial longitudinal slit formed in the foot.

2. Prior Art

Many individuals have lost a limb for various reasons including war, accident, or decease. In most instances these individuals are not only able to live relatively normal lives, but physically active lives as well. Often times, these is individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot—movement of the ankle or foot as it relates to walking or running. Few designs consider the workings of the toes or the less conspicuous movements of the foot and ankle, such as the rotation of the foot and toes when the user stands on an incline. In a natural foot, the foot and toes rotate to conform to the slope of the terrain. The artificial foot of previous designs usually incorporates a unitary foot and toe platform that is incapable of such independent rotational movement or response.

U.S. Pat. No. 5,037,444 issued Aug. 6, 1991 to Phillips discloses a prosthetic foot having a forefoot portion and a heel portion. The forefoot portion has an attachment section, a curvilinear spring section, an arch section, and a toe section formed integrally with one another. The heel portion is removably attached to the forefoot portion at the intersection of the arch and toe sections by a bolt and nut. An elastomeric wedge is inserted between the forefoot portion and the heel portion.

One problem with this configuration is that the forefoot portion, together with the heel portion, form a unitary member incapable of providing independent and multiple responses to uneven terrain, such as a slope. The unitary member is a platform that must rotate as a single body to conform to the slope of the terrain in an unnatural manner. Such a foot is incapable of rotating about a longitudinal axis.

In addition, the forefoot portion and heel portion are attached by a bolt and nut through a bore. Such a bore in a structural member or spring member causes stress concentrations in the material which can lead to catastrophic failure.

The heel portion acts as a lever. When in use, all the weight of the wearer is placed on the heel as the users steps forward. The elastomeric wedge, or the contact between the heel portion and the forefoot portion, acts as a fulcrum at a position between the two ends of the heel portion. Yet the other end of the heel portion is bolted to the forefoot portion. Therefore, a large stress is caused at the connection end of the heel portion which is concentrated at the bore and may break the heel portion.

Furthermore, a shear stress is placed on the bolt because the forefoot and heel portions tend to slide with respect to each other. The tendency to slide also concentrates the force applied by the user (static weight and dynamic walking) in the small area around the bore.

Finally, the attachment section of the forefoot section is a plate with a centered bore. There is no structure or means to adjust the angle of the prosthetic foot with respect to an ancillary socket or the angle at which the prosthetic foot contacts the ground.

U.S. Pat. No. 4,547,913 issued Oct. 22, 1985 to Phillips discloses a prosthetic foot having a forefoot portion and a heel portion. The forefoot portion and the heel portion are bound together with a "resin impregnated filament binding" by winding the filament around the members. Problems with this type of joining technique are (i) the lack of strength in the connection to resist shear forces and (ii) the vulnerability of the connection to shear stress The real strength of fibers is their tensile strength, or the strength of the fibers under loads along the length of the fibers. Thus, filaments circularly wound around two members would be most successful in resisting tensile forces pulling the two members apart. The filaments would be less successful in resisting shear forces sliding or twisting the two members apart Because the foot is subject to so many different forces in many different directions, it is critical that structural or spring members be attached by a method capable of withstanding the numerous applied forces.

U.S. Pat. No. 2,640,200 issued Jun. 2, 1953 to Wisbrun discloses a prosthetic foot having a steel, horizontal foot plate connected to a vertical leg post by two joints. The first joint has a head mounted in a diagonally mounted cylindrical bearing such that as the foot plate rotates downward it is also rotated inward and vis versa. The second joint permits limited vertical rotation by a T-head inserted through a slot, turned, and secured by a screw. An arm, attached to the leg post, extends over the foot plate and engages an inclined leaf spring. The purpose of the above construction is a more natural gait. The resulting motion of the above construction is the rotation of the foot plate down and inward as the user steps on the heel and then rotation upward and outward as weight is taken off the foot plate. Wisbrun also discloses that a slit may be provided in the forward end of the foot plate for "a more effective resilient up-thrust" as weight is taken off the foot plate. One problem with this configuration is the complexity of the several joints. There are numerous moving parts and joints subject to friction, wear, and failure In addition, the slit in the foot plate does not simulate toe rotation.

U.S. Pat. No. 2,036,830 issued Apr. 7, 1936 to Rowley discloses a prosthetic foot having a shin member connected to a foot member by a bearing hinge. The foot member has a solid, inner core portion and a flexible exterior. The foot member also has a rigid member with a "pair of spaced apart prongs" extending between the core and the exterior and a pivot at the ball of the foot in contact with the prongs. The rigid member is operatively attached to a rubber block that expands and contracts between the shin member and core member as the user walks. Thus, the rigid member acts as a lever extending from the toe position to the ankle position and pivoting at the ball of the feet. As the user pivots forward on the foot, the rubber block is compressed and the ankle end of the rigid member is forced down and the toe end of the rigid member is forced up. As the user lifts the foot, the rubber block expands and the ankle end of the rigid member is forced up and the toe end of the rigid member is forced down. The purpose of the rigid member is to return the flexible toe portion to its normal position after being bent upwards by walking. One problem with this configuration is that the rigid prongs do not deflect or bend to simulate toe rotation. Nor do the rigid prongs pivot independently.

Therefore, it would be advantageous to develop a prosthetic foot capable of simulating the natural toe rotation of a real foot. It would also be advantageous to develop a prosthetic foot having a connection between the forefoot member and heel member capable of resisting sliding and twisting. In addition, it would advantageous to develop a prosthetic foot with a means of adjusting the angle at which the foot contacts the ground.

OBJECTS AND SUMMARY OF THE INVENTION

It is an object of the present invention to provide a prosthetic foot capable of simulating the natural rotation of a real foot.

It is another object of the present invention to provide a prosthetic foot with a connection between the forefoot and heel members capable of resisting sliding and twisting.

It is yet another object of the present invention to provide a prosthetic foot with primary and secondary heel members.

It is a further object of the present invention to provide a prosthetic foot with means for adjusting the angle at which the foot contacts the ground.

These and other objects and advantages of the present invention are realized in a prosthetic foot having first and second foot members or a split forefoot member. In the preferred embodiment, the foot, having a forefoot member and a heel member, is comprised of two separate members forming opposite halves of the foot generally about the longitudinal axis of the foot. Although each half may be a mirror image of the other, each may also be configured to accurately reproduce the shape of a natural foot. Because the foot has two halves, or a first and second member, the foot is able to respond to uneven terrain more like a natural foot having rotating toes.

Alternatively, the foot may be a single member having a forefoot member and a heel member and having a slit in a toe portion of the forefoot. The slit separates the toe portion into two protrusions that are better able to simulate natural toe rotation than a prosthetic foot without the slit.

The forefoot member of the foot forms a resilient arc extending from a fixture member to a toe position. The forefoot member has an attachment portion, a curvilinear spring portion, an arch portion, and a toe portion. The heel member extends between the forefoot member and a heel position. The heel member has an attachment portion and a heel portion. The heel member is preferably attached to the forefoot member by wrapping the attachment portion of the heel member and an intersection of the arch and toe portion of the forefoot member with a resin impregnated fibre.

In addition, the foot preferably has a mating means. The mating means may be a rib-and-groove type connection between the forefoot and heel members. The rib-and-groove connection prevents the forefoot and heel portions from sliding and rotating with respect to each other and thus prevents shear stress from being placed on the fibers holding the members together.

The foot has a fixture member for attachment to a socket for receiving a stump of an amputee. The first and second members of the foot, or the forefoot member of the foot, are attached to the fixture member. The fixture member may also include an angle adjustment means for adjusting the angle of the foot members with respect to the ground.

Furthermore, the foot may include a secondary heel member in addition to the heel members or primary heel member. The secondary heel member helps support the primary heel member.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1:
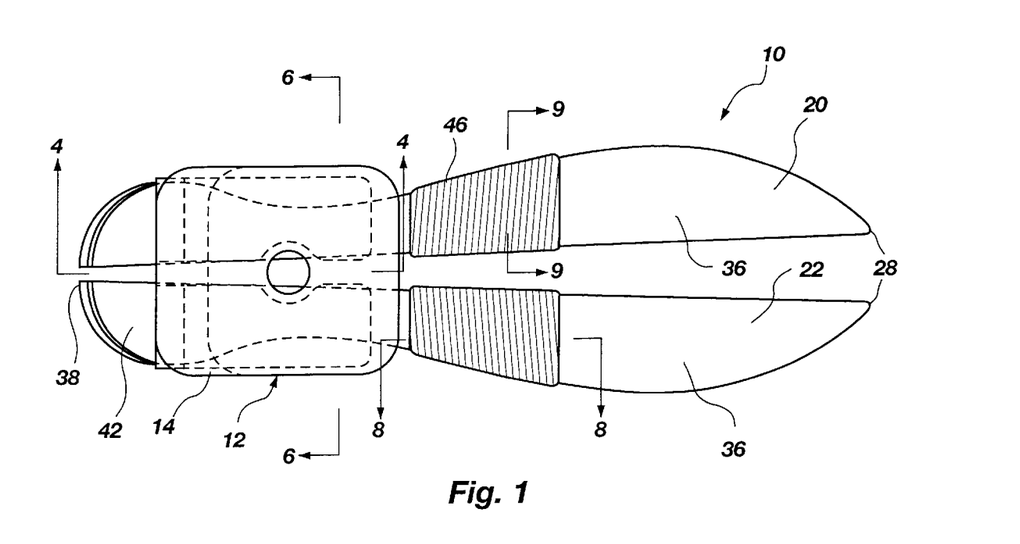
FIG. 1 is a top view of a prosthetic foot incorporating a preferred embodiment of the present invention.
Figure 2:
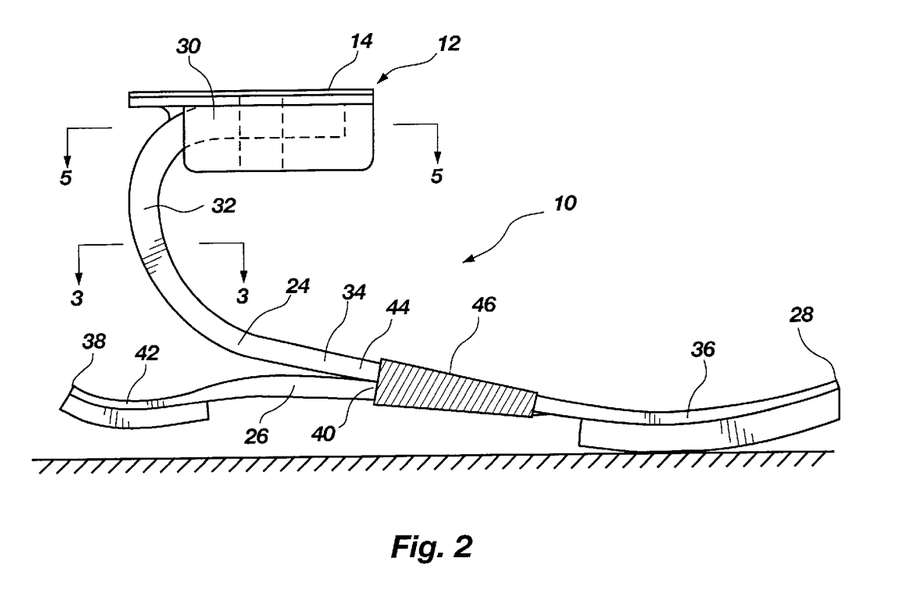
FIG. 2 is a front elevational view of the prosthetic foot incorporating a preferred embodiment of the present invention.

As illustrated in FIGS. 1 and 2, a preferred embodiment of a prosthetic foot 10 of the present invention is shown. The prosthetic foot 10 has a fixture member 12 for attachment to a socket (not shown) for receiving a stump of an amputee. The socket is configured for the specific needs of the amputee but typically has a portion adapted for attachment to a standard fixture, such as fixture member 12. The fixture member 12 has a generally horizontal surface 14 for contacting the socket. The standard fixtures typically have a generally horizontal surface, as shown in FIGS. 1 and 2, or a generally vertical surface (not shown).

In the preferred embodiment, the prosthetic foot 10 has a first member 20 coupled to the fixture member 12 and a second member 22 coupled to the fixture member 12, as shown in FIG. 1. Referring to FIG. 2, the first member 20 and second member 22 have a forefoot member 24 and a heel member 26. The forefoot member 24 forms an arc extending between the fixture member 12 and a toe position 28. The forefoot member 24 has an attachment portion 30 for coupling to the fixture member 12; a curvilinear spring portion 32 extending from the attachment portion 30; an arch portion 34 extending from the spring portion 32; and a toe portion 36 extending from the arch portion 34.

The forefoot member 24 is preferably made of a resilient material. As the amputee steps on the prosthetic foot 10, the forefoot member 24 deflects. Because the forefoot member 24 is made of a resilient material, the forefoot member 24 acts as a spring and stores the energy to be released as the amputee moves forward.

The heel member 26 extends between the forefoot member 24 and a heel position 38. The heel member 26 has an attachment portion 40 and a heel portion 42. The heel member 26 is also made of a resilient material. As the amputee steps on the prosthetic foot 10, the heel member 26 deflects. Because the heel member 26 is made of a resilient material, it acts as a spring and cushions the force of the foot 10 as it contacts the ground.

The heel member 26 is preferable attached to the forefoot member 24 at an intersection 44 between the toe portion 36 and the arch portion 34. In addition, the heel member 26 is preferably attached to the forefoot member 24 by wrapping the attachment portion 40 of the heel member 26 and the intersection 44 with a resin impregnated fibre 46.

Alternatively, the heel member 26 may be attached to the forefoot member 24 by any appropriate means including bolting or even forming the heel member 26 integrally with the forefoot member 24.

Figure 3:
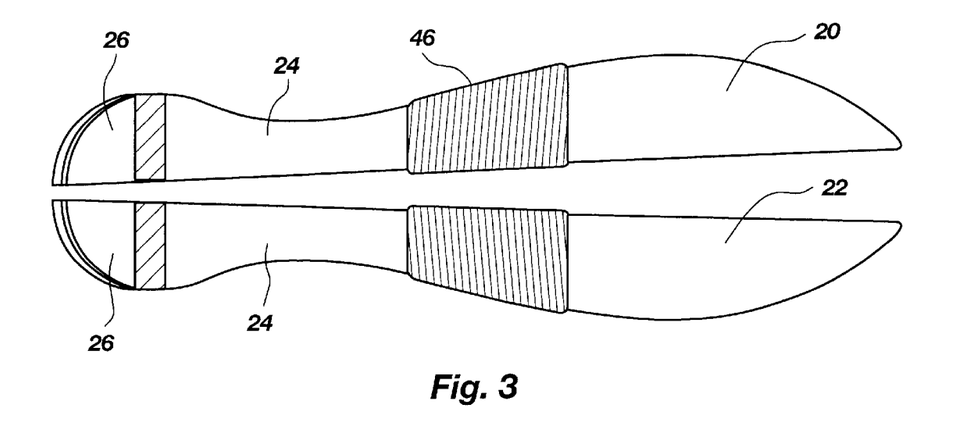
FIG. 3 is a top cross section view of a preferred embodiment of the prosthetic foot of the present invention taken along line 3—3 of FIG. 2.

The second member 22 is disposed adjacent the first member 20. The second member 22 is independently movable with respect to the first member 20. As shown in FIGS. 1 and 3, the second member 22 may be a mirror image of the first member 20. Alternatively, the first and second members 20 and 22 may be configured to resemble an actual foot.

A substantial portion of the foot 10, including the curvilinear spring portion 32, the arch portion 34, the toe portion 36, and the heel portion 42 of the foot 10 are composed of two members 20 and 22. Because the foot 10 is composed of two members 20 and 22, the foot 10 is able to respond to uneven terrain more like a natural foot with rotating toes. In addition, the foot 10 is better able to simulate toe and axial foot rotation.

Figure 4:
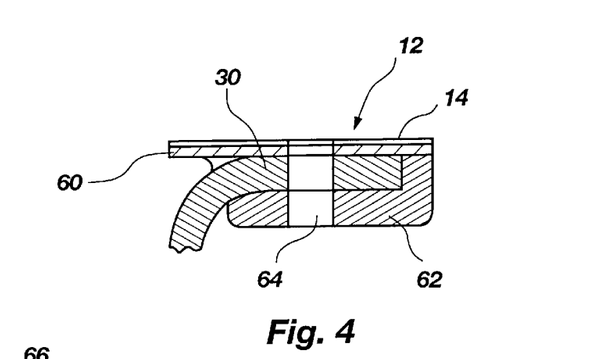
FIG. 4 is a elevational cross section view of a preferred embodiment of a fixture member of the prosthetic foot of the present invention taken along line 4—4 of FIG. 1.
Figure 5:
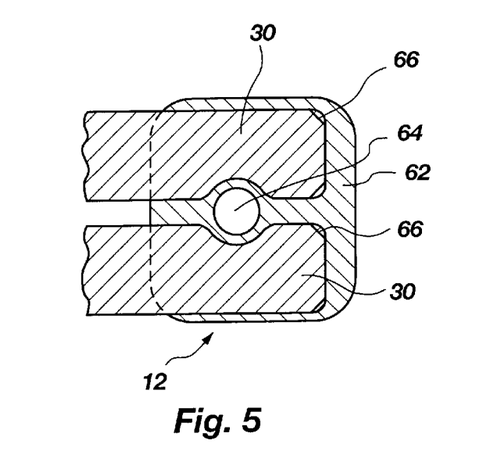
FIG. 5 is a top cross section view of a preferred embodiment of the fixture member of the prosthetic foot of the present invention taken along line 5—5 of FIG. 2.

Referring to FIG. 4, the fixture member 12 has an upper plate 60 and a lower plate 62. The attachment portion 30 of the first and second members 20 and 22 are coupled to the fixture member 12 between the upper and lower plates 60 and 62. A bore 64 passed through the upper and lower plates 60 and 62 so that the fixture member 12 may be attached to a socket (not shown) by a bolt or screw or the like. Referring to FIG. 5, the lower plate 62 has recesses 66 formed therein for receiving the attachment portion 30 of the first and second members 20 and 22. The recesses 66 are formed to hold the attachment portion 30 firmly.

Figure 6:
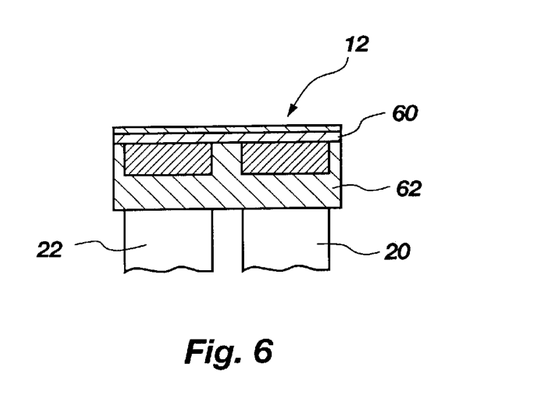
FIG. 6 is a front cross section view of a preferred embodiment of the fixture member of the prosthetic foot of the present invention taken along line 6—6 of FIG. 1.
Figure 7:
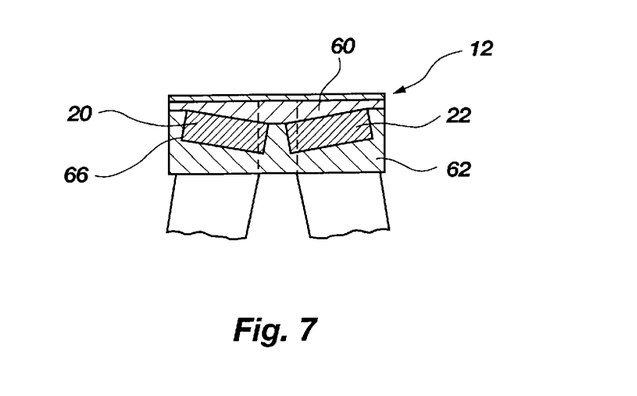
FIG. 7 is a front cross section view of an alternative embodiment of the fixture member of the prosthetic foot of the present invention.

Referring to FIG. 6, the first and second members 20 and 22 are held in the recesses 66 such that the members 20 and 22 are substantially parallel with the ground. Referring to FIG. 7, an alternative embodiment of the fixture member 12 is shown. The fixture member 12 may incorporate an angle adjustment means for adjusting the angle of the forefoot member and/or heel member with respect to the ground As shown in FIG. 7, the recesses 66 formed in the lower plate 62 may have an angle so that the first and second members 20 and 22 are at an angle with respect to the fixture member 12 and the ground.

Figure 8:
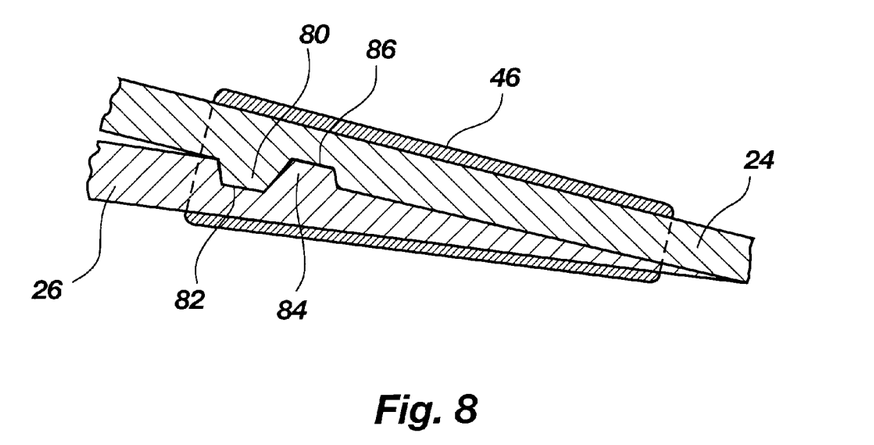
FIG. 8 is an elevational cross section view of a preferred embodiment of a rib-and-groove mating means of the prosthetic foot of the present invention taken along line 8—8 of FIG. 1.
Figure 9:
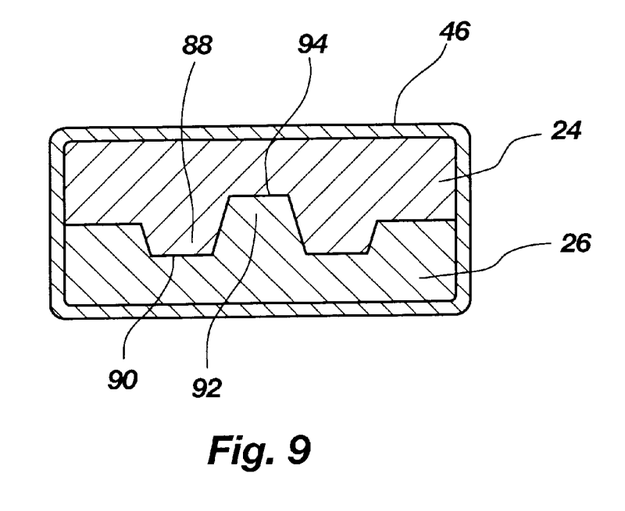
FIG. 9 is an elevational cross section view of a preferred embodiment of the rib-and-groove mating means of the prosthetic foot of the present invention taken along line 9—9 of FIG. 1.

As illustrated in FIGS. 8 and 9, the forefoot member 24 and the heel member 26 have a mating means. The forefoot and heel members 24 and 26 are preferably attached by a resin impregnated fibre 46. The tensile strength of this attachment, or the strength of the fibres along its length, is very strong. So the attachment is able to resist forces tending to pull the members apart. Fibres, however; lack strength in resisting shear forces. Thus the filaments would be less successful in resisting shear forces tending to slide the two members apart. Because a prosthetic foot is subject to many different forces in many different directions, it is critical that the members be attached by a method capable of withstanding the numerous applied forces.

Preferably, the mating means is a rib-and-groove type attachment between the forefoot member 24 and the heel member 26. Referring to FIG. 8, a lateral rib 80 formed in the forefoot member 24 mates with a lateral groove 82 formed in the heel member 26. It is of course understood that a rib 84 may be formed in the heel member 26 to mate with a groove 86 formed in the forefoot member 24 or that there may be multiple ribs and grooves formed in either member. The ribs 80 and 84 and the grooves 82 and 86 are formed laterally with respect to the foot 10. This prevents twisting and longitudinal sliding between the forefoot member 24 and the heel member 26.

Referring to FIG. 9, a longitudinal rib 88 formed in the forefoot member 24 mates with a longitudinal groove 90 formed in the heel member 26. It is of course understood that a rib 92 may be formed in the heel member 26 to mate with a groove 94 formed in the forefoot member 24 or that there may be multiple ribs and grooves formed in either member. The ribs 88 and 92 and the grooves 90 and 94 are formed longitudinally with respect to the foot 10. This prevents twisting and lateral sliding between the forefoot member 24 and the heel member 26.

Figure 10:
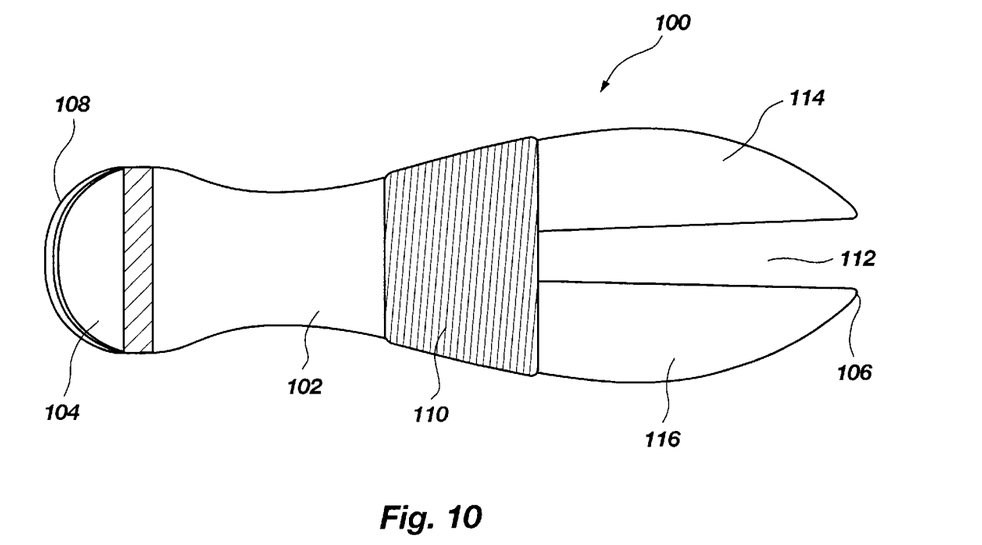
FIG. 10 is a top cross section view of an alternative embodiment of the prosthetic foot of the present invention.

As illustrated in FIG. 10, an alternative embodiment of a prosthetic foot 100 of the present invention is shown. The foot 100 has a forefoot member 102 and a heel member 104. The forefoot member 102 forms an arc extending between the fixture member (not shown) and a toe position 106. Like the preferred embodiment, the forefoot member 102 has an attachment portion, a curvilinear spring portion, an arch portion and a toe portion.

The heel member 104 extends between the forefoot member 102 and a heel position 108. Like the preferred embodiment, the heel member 108 has an attachment portion and a heel portion.

The heel member 104 is preferable attached to the forefoot member 102 at an intersection between the toe portion and the arch portion. In addition, the heel member 104 is preferably attached to the forefoot member 102 by wrapping the attachment portion of the heel member 102 and the intersection with a resin impregnated fibre 110.

A slit 112 is formed in the forefoot member 102 extending from an open end at the toe position 106 to at least the heel portion 104. Because the forefoot member 102 has a slit 112, the toe portion of the forefoot member 102 is divided into a first protrusion 114 and a second protrusion 116. The two protrusions 114 and 116 allow the foot 100 the ability to respond to uneven n terrain more like a natural foot with rotating toes.

Figure 11:
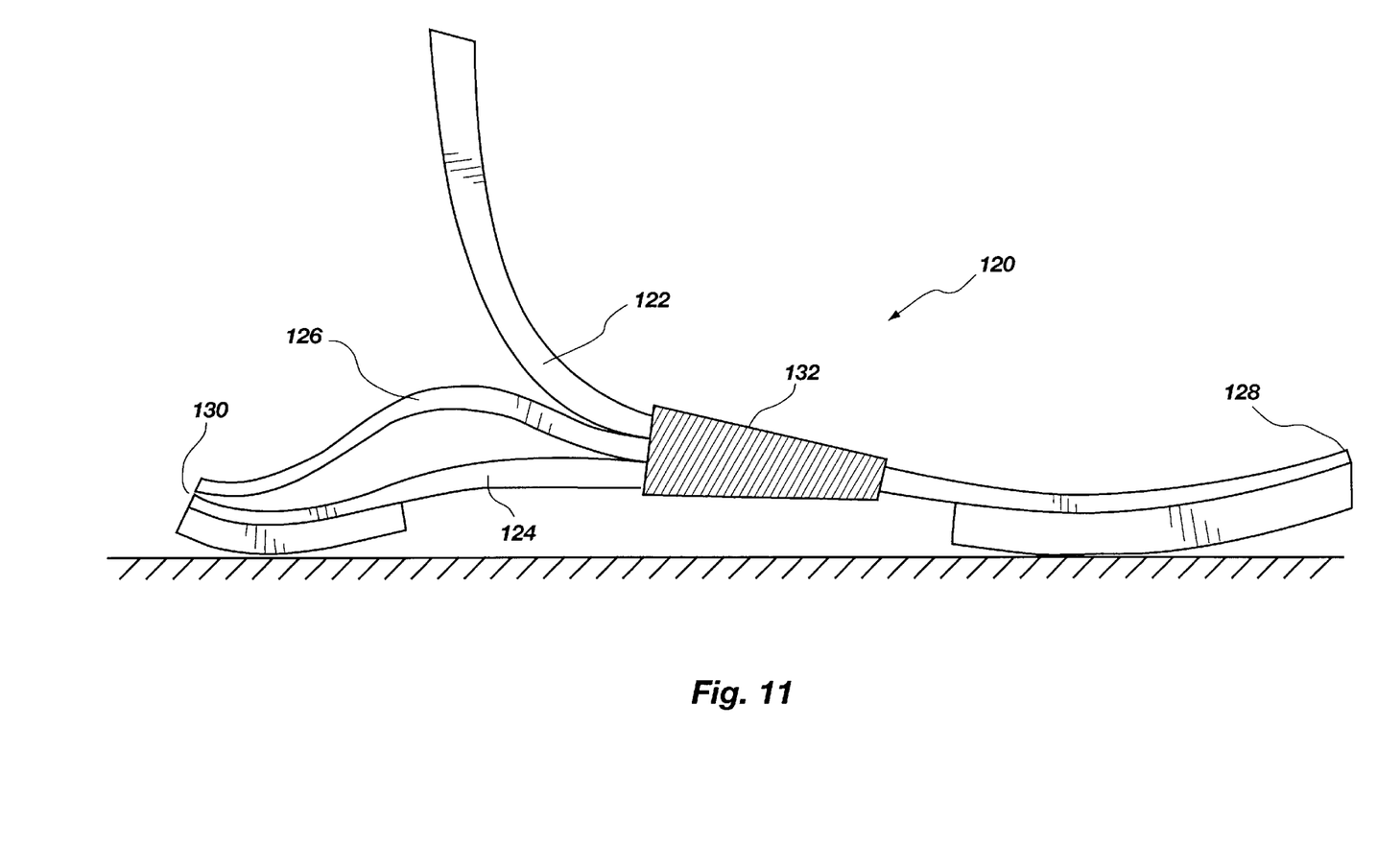
FIG. 11 is an elevational view of an alternative embodiment of a prosthetic foot of the present invention.

As illustrated in FIG. 11, an alternative embodiment of a prosthetic foot 120 of the present invention is shown. The prosthetic foot 120 has a fixture member (not shown) for attachment to a socket (not shown) for receiving a stump of an amputee. The prosthetic foot 120 has a forefoot member 122, a heel member 124, and a secondary heel member 126. The forefoot member 122 forms an arc extending between the fixture member and a toe position 128. Like the preferred embodiment, the forefoot m ember 122 has an attachment portion, a curvilinear spring portion, an arch portion, and a toe portion.

The primary heel member 124 extends between the forefoot member 122 and a heel position 130. Like the preferred embodiment, the heel member 124 has an attachment portion and a heel portion. The secondary heel member 126, likewise extends between the fore foot member 122 and the heel position 130. The first and second heel members 124 and 126 are made of a resilient material. As the amputee steps on the prosthetic foot 120, the heel members 124 and 126 deflect. The secondary heel member 126 provides added support to the first heel member 124.

The first and second heel members 124 and 126 are preferable attached to the forefoot member 122 at an intersection between the toe portion and the arch portion. In addition, the heel members 124 and 126 are preferably attached to the forefoot member 122 by wrapping the attachment portion of the heel members 122 and 126 and the intersection with a resin impregnated fibre 132.

Both the heel members 124 and 126 may incorporate a mating means as in the preferred embodiment. A rib-and-groove type attachment may be used between the forefoot member 122 and the secondary heel 126 member and between the secondary heel member 126 and the primary heel member 124.

Alternatively, the second heel member 126 may be replaced by a resilient member such as rubber or the like.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

What is claimed is:

1. A prosthetic foot configured to be attached to a fixture member, comprising:
   an elongated resilient forefoot member forming a resilient arc extending between a fixture location and a toe position, the forefoot member having an attachment portion configured to attach to the fixture member, a curvilinear spring portion extending from the attachment portion, ail arch portion extending from the spring portion, and a toe portion extending from the arch portion to the toe position;
   a resilient heel member, attached to the forefoot member and extending to a heel position, the heel member having an attachment portion attached to the forefoot member at an attachment location near the arch portion of the forefoot member, and a heel portion extending from the attachment portion to the heel location;
   a mating rib and groove, formed in the forefoot and heel members at the attachment location, configured to prevent the forefoot and heel members from twisting or sliding with respect to one another; and
   a resin impregnated fiber, wrapped around the forefoot and heel members at the attachment location, to attach the heel member to the forefoot member.

2. The prosthetic foot of claim 1, further comprising:
   a secondary heel member attached to the forefoot member between the forefoot member and the heel member, the secondary heel member forming a resilient arc extending between the forefoot member and a heel position.

3. The prosthetic foot of claim 1, further comprising:
   an angle adjustment means for adjusting the angle of the forefoot member with respect to the fixture member and the ground.

4. The prosthetic foot of claim 1, further comprising:
   a slit formed in the forefoot member, the slit extending from an open end at the toe position to at least the heel member, the slit forming a first protrusion and a second protrusion in the forefoot member.

5. A prosthetic foot in accordance with claim 1, wherein the rib and groove are oriented longitudinally to resist lateral sliding between the forefoot and heel members.

6. A prosthetic foot in accordance with claim 1, wherein the rib and groove are oriented laterally to resist longitudinal sliding between the forefoot and heel members.

7. A prosthetic foot in accordance with claim 1, wherein the groove is formed in the forefoot member at the attachment location; and wherein the rib is formed in the attachment portion of the heel member.

8. A prosthetic foot in accordance with claim 1, wherein the groove is formed in the attachment portion of the heel member; and wherein the rib is formed in the forefoot member at the attachment location.

9. A prosthetic foot in accordance with claim 1, wherein the groove includes grooves formed in both the attachment portion of the heel member and the forefoot member at the attachment location; and wherein the rib includes ribs formed in both the forefoot member at the attachment location and the attachment portion of the heel member.

10. A prosthetic toot simulating toe and related axial foot rotation, comprising:
    a fixture member;
    a first member coupled to the fixture member, the first member having a forefoot member and a heel member, this forefoot member forming a resilient arc extending between the fixture member and a toe position and including a arch portion between the fixture member aid the toe position, the heel member extending between the forefoot member and a heel position and attaching to the forefoot member at an attachment location, near the arch portion of the forefoot member;
    a second member independently moveable with respect to the first member and coupled to the fixture member adjacent the first member, the second member having a forefoot member and a heel member, the forefoot member forming a resilient arc extending between the fixture member and a toe position and including a arch portion between the fixture member and the toe position, the heel member forming a resilient arc extending between the forefoot member at a heel position and attaching to the forefoot member at an attachment location near the arch portion of the forefoot member;

a rib-and-groove attachment between each of the forefoot and heel members at the attachment location including a mating rib and groove formed in the forefoot and heel members configured to prevent the forefoot and heel members from twisting or sliding with respect to one another; and a resin impregnated fiber, wrapped around each of the forefoot and heel members at the attachment location, to attach the heel member to the forefoot member.

11. The prosthetic foot of claim 10, further comprising:

a secondary heel member coupled to the forefoot member between the forefoot member and the heel member, the secondary heel member forming a resilient arc extending between the forefoot member and a heel position.

12. The prosthetic foot of claim 10, further comprising:

an angle adjustment means for adjusting the angle of the forefoot member with respect to the fixture member and the ground.

13. A prosthetic foot in accordance with claim 10, wherein the rib and groove are oriented longitudinally to resist lateral sliding between the forefoot and heel members.

14. A prosthetic foot in accordance with claim 10, wherein the rib and groove are oriented laterally to resist longitudinal sliding between the forefoot and heel members.

15. A prosthetic foot in accordance with claim 10, wherein the groove is formed in the forefoot member at the attachment location; and wherein the rib is formed in the attachment portion of the heel member.

16. A prosthetic foot in accordance with claim 10, wherein the groove is formed in the attachment portion of the heel member; and wherein the rib is formed in the forefoot member at the attachment location.

17. A prosthetic foot in accordance with claim 10, wherein the groove includes grooves formed in both the attachment portion of the heel member and the forefoot member at the attachment location; and wherein the rib includes ribs formed in both the forefoot member at the attachment location and the attachment portion of the heel member.

* * * * *